United States Patent [19]

Schmidt

[11] Patent Number: 4,957,496
[45] Date of Patent: Sep. 18, 1990

[54] SLOTTED SLIDE PLATE ASSEMBLY FOR OSTEOSYNTHESIS

[75] Inventor: Joachim Schmidt, Cologne, Fed. Rep. of Germany

[73] Assignee: Mecron medizinische Produkte GmbH, Berlin, Fed. Rep. of Germany

[21] Appl. No.: 434,463

[22] Filed: Nov. 13, 1989

[30] Foreign Application Priority Data

Nov. 11, 1988 [DE] Fed. Rep. of Germany ....... 3838774

[51] Int. Cl.$^5$ .............................................. A61F 2/00
[52] U.S. Cl. ......................................... 606/70; 606/71
[58] Field of Search ..................... 606/69, 70, 71, 54, 606/53, 105, 86; 128/334 R, 334 C

[56] References Cited

U.S. PATENT DOCUMENTS

| | | | |
|---|---|---|---|
| 1,025,008 | 4/1912 | Miner | 606/71 |
| 2,486,303 | 10/1949 | Longfellow | 606/71 |
| 3,528,085 | 9/1970 | Reynolds | 606/69 |
| 3,596,656 | 8/1971 | Kaute | 606/71 |
| 3,604,414 | 9/1971 | Borges | 606/71 |
| 3,659,595 | 5/1972 | Haboush | 606/71 |
| 4,297,993 | 11/1981 | Härle | 606/70 |
| 4,338,926 | 7/1982 | Kummer | 606/70 |
| 4,513,744 | 4/1985 | Klaue | 606/69 |

FOREIGN PATENT DOCUMENTS

| | | |
|---|---|---|
| 0201023 | 11/1986 | European Pat. Off. . |
| 2808971 | 9/1979 | Fed. Rep. of Germany . |
| 2911386 | 6/1980 | Fed. Rep. of Germany . |
| 373516 | 1/1964 | Switzerland . |
| 462375 | 10/1968 | Switzerland . |

Primary Examiner—Robert A. Hafer
Assistant Examiner—Michael A. Brown
Attorney, Agent, or Firm—Spencer & Frank

[57] ABSTRACT

A slotted slide plate assembly for setting bones in a fracture area and exerting a pressure in a predetermined direction to obtain a bone compression includes a first plate element adapted for a face-to-face engagement with a bone surface; a second plate element adapted for a face-to-face engagement with the topside of the first plate element; a securing device which prevents a relative displacement between the first and second plate elements when they are in a face-to-face engagement with one another; and first and second slide slots provided in the first and second plate elements, respectively, and being oriented parallel to the predetermined direction. The two slide slots are overlapping when the two plate elements engage one another. Each slide slot has sloping slide ramps arranged such that the slide ramp in the first plate element is a continuation of the slide ramp in the second plate element. Thus, a tightening screw inserted through the two slide slots from the topside of the upper, second plate element slides, while being screwed into the bone, with a screw head on the slide ramp provided in the second plate element and subsequently slides on the slide ramp provided in the first plate element.

9 Claims, 2 Drawing Sheets

SLOTTED SLIDE PLATE ASSEMBLY FOR OSTEOSYNTHESIS

CROSS REFERENCE TO RELATED APPLICATION

This application claims the priority of Federal Republic of Germany Application No. P 38 38 774.3 filed Nov. 11th, 1988, which is incorporated herein by reference.

BACKGROUND OF THE INVENTION

This invention relates to slotted slide plates used in osteosynthesis for repositioning (setting) fractured bones. The plates cause a relative displacement between adjacent bone parts by virtue of a camming effect between sloping slide ramps flanking the plate slot and the head of a screw which passes through the plate slot and is screwed into the bone.

The principle of the slotted slide plates is based on the longitudinal displaceability of the fractured bone parts in the direction of the fracture, whereby a compression effect is achieved. The lowering of the screw head into the slot forces a shift of the broken bone parts.

Slotted slide plates of the above-outlined type are known in a great number of varieties for various fractures, including splinter fractures. In this connection, reference is made to "Osteosynthesepraxis" (Osteosynthesis in Practice) by Frank Schauwecker, published in 1981 by Georg Thieme Verlag, Stuttgart/New York.

The order of magnitude of the achievable displacement paths depends from the thickness of the slotted slide plate and from the slope angle of the slide ramp engaged by the screw head. Both parameters, however, are limited for medical and geometrical reasons. Therefore, subsequent tightening by means of a plate tightening tool can often not be avoided. Such an externally applied plate tightening tool is, however, disadvantageous, in that it tends to enlarge the wound area and might make additional bone drilling necessary. Furthermore, the prolonged time needed to perform the surgery is also a drawback.

SUMMARY OF THE INVENTION

It is an object of the invention to provide an improved slotted slide plate of the above-outlined type from which the discussed disadvantages are eliminated; that is, which makes possible a significantly lengthened displacement path and ensures a sufficiently high bone compression over the entire displacement path.

This object and others to become apparent as the specification progresses, are accomplished by the invention, according to which, briefly stated, the slotted slide plate assembly for setting bones in a fracture area and exerting a pressure in a predetermined direction to obtain a bone compression includes a first plate element adapted for a face-to-face engagement with a bone surface; a second plate element adapted for a face-to-face engagement with the topside of the first plate element; a securing device which prevents a relative displacement between the first and second plate elements when they are in a face-to-face engagement with one another; and first and second slide slots provided in the first and second plate elements, respectively, and being oriented parallel to the predetermined direction. The two slide slots are overlapping when the two plate elements engage one another. Each slide slot has sloping slide ramps arranged such that the slide ramp in the first plate element is a continuation of the slide ramp in the second plate element. Thus, a tightening screw inserted through the two slide slots from the topside of the upper, second plate element slides, while being screwed into the bone, with a screw head on the slide ramp provided in the second plate element and subsequently slides on the slide ramp provided in the first plate element.

Thus, according to the invention, a first, or lower plate element is provided which lies on the bone and which conforms to the shape thereof. Further, a second, or upper plate element is provided which is immovably but releasably connected face-to-face with the lower plate element. The multipart (preferably two-part) slotted slide plate assembly results in an increase of the overall thickness (common thickness) which, however, is reduced to a single plate thickness upon completion of the tightening procedure by removing the upper plate element, thus leaving in the patient's body only the lower plate element (bone plate). The increase in thickness of the plate assembly makes possible a lengthening of the slide ramps and thus a lengthening of the displacement path of the tightening screw which passes through aligned slide slots in both plates. In particular, despite the normal thickness of the bone plate which remains in the patient, sufficiently high bone compression may be exerted throughout the entire extended displacement path. The slide slots in the two plate elements are so configured that upon superposition of the plate elements, a constant-slope or a varying-slope slide ramp for the underface of the screw head is obtained. The slot of the upper plate element is preferably provided with an enlarged aperture at the end of the slide ramp of the upper plate (at the location of transition to the slide ramp of the lower plate) to allow therethrough full passage of the entire screw.

The cross section of the slide ramp corresponds to the underside of the screw head essentially over the entire length of the slide ramp to thus ensure a superior guidance for the screws.

The underside of the lower plate element conforms to the transverse curvature of the bone to be treated. In case of a constant thickness of the lower plate element, this results in a similar curvature in the upper plate element in the transverse direction. The upper plate element, in the zone of its underside, conforms to the shape of the upper side of the lower plate element.

To optimize the bone compression in case of intertrochanteric osteotomies, the lower plate element (which lies on the bone) has an angular bend at one end. It is feasible, however, to use other shapes such as curved configurations for special applications in which case the upper plate is accordingly made to conform to the lower plate.

To ensure an increase in the stability of the achieved fixation and thus a lengthening of the displacement path, the lower plate element may be provided with further slide slots with slide ramps which, however, do not have corresponding slide ramps in the upper plate element. By providing slide slots for sequential use, the displacement paths are added; a predetermined screw engagement sequence, however, has to be observed. The slide slots in the plate elements have such a length that at the end of the slide ramp the screws which have to be tightened first still have a sufficient displacement path (with only a slight inclination) to take up the relative sliding motion between the bones and the plate effected by tightening the screws in the additional slide slots.

After tightening the screw or screws along the common slide ramp or ramps, the overlying upper plate element may be removed from the lower plate element to which it was immovably secured. Such a removal exposes and thus renders accessible the additional slide slots in the lower plate element.

A significant advantage involved with the removability of the upper plate element from the medical point of view resides in that despite the enlargement of the slide path and the resulting lengthening of the achievable fixing path, there is no increase in the thickness of the plate element which remains in the patient's body.

The removed upper plate element may be re-used with the lower plate elements. The necessary sterilization can be carried out in a simple manner due to the simplicity of the component.

By virtue of the slide ramps formed by the slide ramp parts in one or more slide slot pairs (wherein the two slide slots forming one pair are provided in the upper and lower plate elements, respectively) it is possible to provide an angle plate with slide slots with which, due to the lengthened displacement paths, a sufficiently high bone pressure can be exerted over the entire displacement path for a highly satisfactory treatment of fractures. Despite such a significant advantage, there is no thickness increase of the slotted slide plates which remain in the patient's body, as compared to the thickness of conventional slide plates.

BRIEF DESCRIPTION OF THE DRAWING

FIG. 1a is a sectional view, taken along line 1a—1a of FIG. 1.

DESCRIPTION OF THE PREFERRED EMBODIMENT

Figure 1:
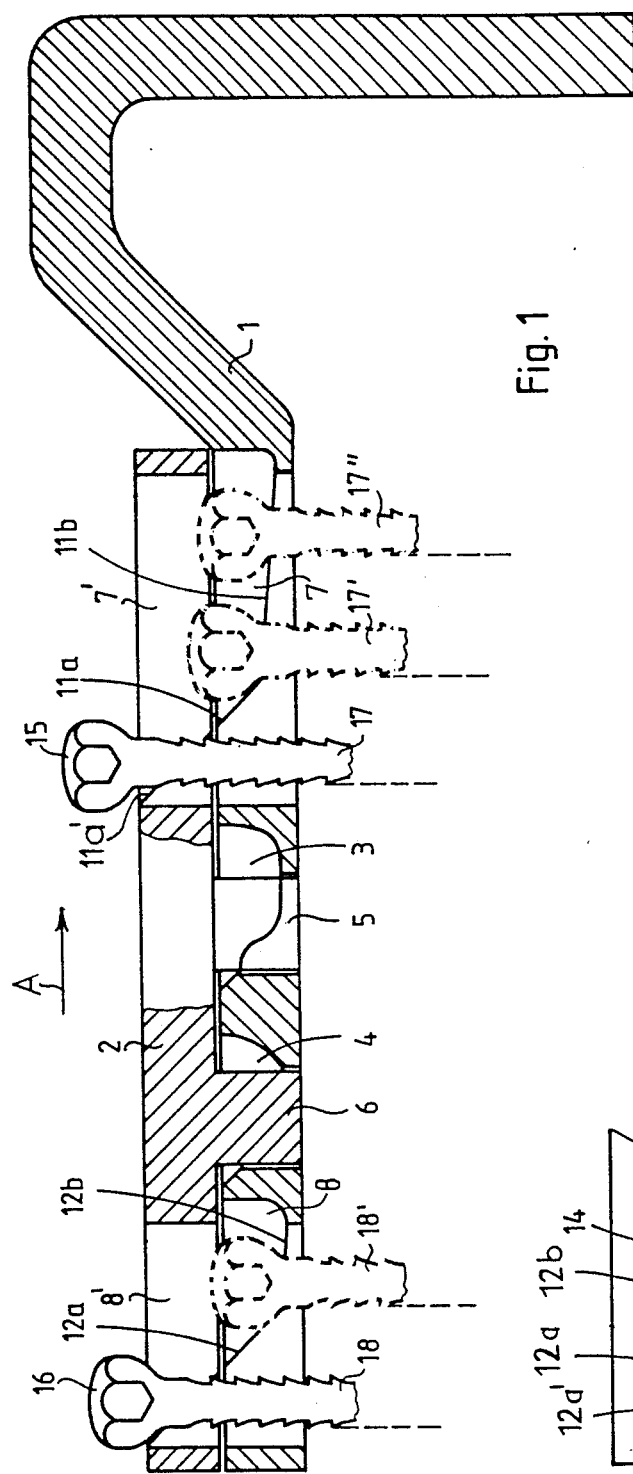
FIG. 1 is a sectional side elevational view of a preferred embodiment of the invention.

Turning to FIG. 1, the preferred embodiment illustrated therein comprises an angled lower plate element 1 and an upper plate element 2. The plates 1 and 2 are coupled to one another such that at least in the direction of bone compression A the two plates 1 and 2 cannot move relative to one another, that is, a force exerted on the plate 1 in that direction is positively transmitted to the plate 2. To obtain such a force-transmitting coupling, the lower plate 1 is provided with two apertures 3 and 4 (which, as will be described later, also serve as slide slots), into which fit respective projections 5 and 6 of the upper plate 2.

The two plate elements 1 and 2 are provided with a first slot pair formed of aligned slide slots 7 (in plate 1) and 7' (in plate 2) and a second slot pair formed of aligned slide slots 8 (in plate 1) and 8' (in plate 2). Within the slide slot 7 in the plate element 1 there is provided a sloped slide ramp 11a which is adjoined by a slide ramp 11b of lesser slope. In the slide slot 7' in the plate element 2 there is situated a slide ramp 11a ' which, when the two plates 1 and 2 are connected to one another, is aligned and is contiguous with the slide ramp 11a provided in the slide slot 7 of plate 1. Similarly, in the slide slot 8 of plate 1 there is provided a sloped slide ramp 12a which is adjoined by a slide ramp 12b of lesser slope. In the slide slot 8' of the upper plate element 2 there is situated a slide ramp 12a' which, when the two plates 1 and 2 are connected to one another, is aligned and contiguous with the slide ramp 12a. Thus, viewing the two slide slots 7, 7' together, throughout their entire length there extends the slide ramp formed of consecutive parts 11a', 11a and 11b, and similarly, viewing the slide slots 8, 8' together, there extends through the entire length thereof a sloped slide ramp oriented and inclined downwardly in the direction A and formed of consecutive parts 12a', 12a and 12b. The slide ramps in each slot pair are provided along the opposite longitudinal edges of the slot as may be observed in FIG. 2. The slide ramps 11b and 12b which have the lesser slope and which are formed in the lower plate 1, correspond in their length to the total length of all slide ramps which, according to the predetermined sequence of screw engagement, are sequentially provided with tightening screws.

The slide ramp 11b in the slide slot 7 is significantly longer than the slide ramp 12b in the slide slot 8 because, as will be described later, first a screw is inserted into the slot pair 7, 7' to cooperate with the slide ramps 11a', 11a, 11b and only thereafter is a screw inserted into the slide slot pair 8, 8' to move on the slide ramp 12a', 12a, 12b. Upon tightening of the screw in the slide slot pair 8, 8', the screw previously inserted into the slide slot pair 7, 7' is also displaced along its slide ramp 11b so that the displacement part which is achieved along the slide ramp 11b is obtained as the sum of the displacement parts along the slide ramps 12a', 12a, 12b.

As seen in FIG. 1a, the upper plate element 2, in the zone of its underside, conforms to the shape of the upper side of the lower plate element 1.

Figure 2:
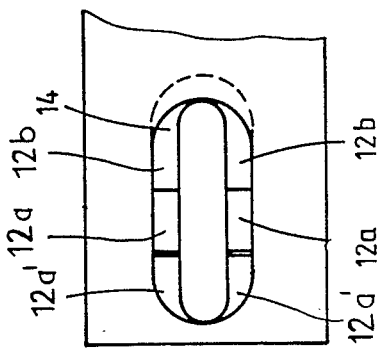
FIG. 2 is a fragmentary top plan view of a terminal part of the preferred embodiment.

As shown in FIG. 2, the upper plate element 2 is, within the slide slots 7' and 8', provided, at the end of the respective slide ramp 11a' and 12a', with an enlarged aperture 14 for allowing the passage of the screw head 15 and 16, respectively.

The slide slot pair 7, 7', situated at the implant-side, is designed for a displacement path of approximately 8 mm (that is, 3 mm along the slide ramps 11a', 11a, plus 3 mm+1 mm+1 mm along the slide ramp 11b), whereas the slide slot pair 8, 8', which is remote from the implant, is designed for a displacement path of approximately 5 mm (that is, 3 mm along the slide ramps 12a', 12a plus 1 mm+1 mm along the slide ramp 12b).

First, a screw 17 is, with the aid of an eccentric boring template, positioned at the outermost end of the slide slot pair 7, 7'. Upon tightening the screw 17 a tightening path of 3 mm is achieved as the screw head 15 travels down the slide ramps 11a', 11a. After such tightening, the screw 17 assumes its phantom-line position 17'. Thereafter, the screw 18 is inserted with the help of an eccentric boring template at the outer end of the slide slot pair 8, 8'. Upon tightening of the screw 18, the latter, similarly to the screw 17, travels down the slide ramps 12a', 12a and thereby achieves a tightening path of approximately 3 mm. During this occurrence, the screw 17 is also displaced 3 mm until it assumes the phantom-line position 17. Thus, altogether a tightening displacement of 6 mm=3 mm+3 mm is carried out.

The underside of the screw heads 15 and 16 has a hemispherical configuration, and thus its area of contact with the slide ramps is optimized by comprising between a good form fit and an easy tightening procedure.

For enhancing such a result, the longitudinal edges of the slide ramps are chamfered.

After the screw 17 has reached its position 17' and, at the same time, the screw 18 has reached its position 18', the upper plate element 2 may be removed by an appropriate tool, whereupon the slide slots 3 and 4 of the lower plate element 1 are exposed and become accessible. Applying additional screws (not shown) through the slide slots 3 and 4 increases stability and makes possible a further, additional approach of the fractured bone portions through a path of approximately 1 mm each. Upon tightening the screw within the slide slot 3, the screw is displaced approximately 1 mm in the direction of the bone fracture, and, simultaneously, the screws 17 and 18 travel an additional path of the same length. The screw to be tightened subsequently in the slide slot 4 effects a further displacement of 1 mm, causing all previously inserted screws to travel the same path along their respective slide slots. The achieved total tightening is thus approximately 8 mm=6 mm+1 mm+1 mm.

Figure 3:
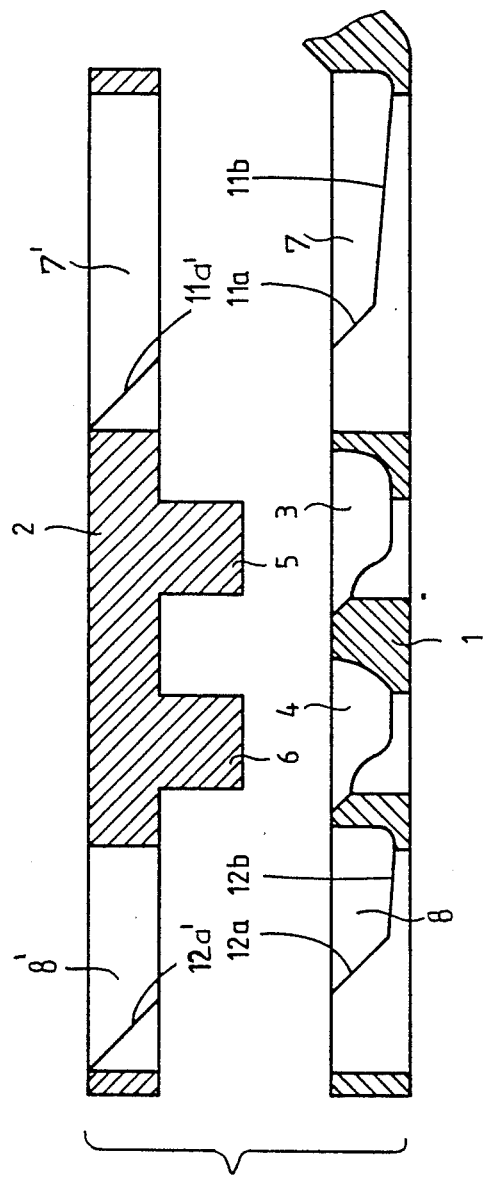
FIG. 3 is a sectional elevational view of two components of the preferred embodiment, illustrated in a separated state.

Turning to FIG. 3, there are shown therein the plate elements 1 and 2 in a separated position. In this Figure, particularly the shape of the projections 5 and 6 can be clearly seen, which are complemental in form to the shape of the apertures formed by the slide slots 3 and 4. FIG. 3 furthermore shows that the bone plate (lower plate) 1 may be a symmetrical flat plate rather than of angled construction as shown in FIG. 1. A part which corresponds in mirror symmetry fashion to the illustrated portion joins the other side of the symmetry line B shown in dash-dotted lines.

By connecting the two plate elements 1 and 2 to one another, the bone securing system obtains the necessary thickness for achieving a lengthened tightening path and the required bone compression. Also, the stability of the system is increased. In the preferred embodiment described, an increased tightening path with slide slots may be achieved without disadvantageous effects on the usefulness of an angled plate. The implanted flange blade corresponds in size and stability to angle plates used heretofore. The shaft, which for structural reasons is about 9 mm longer, has no disadvantageous effect.

By eliminating the use of an external plate tightener which, in the prior art arrangements, caused an enlarged wound area and made necessary an additional bone drilling, surgery is facilitated and its duration shortened.

It will be understood that the above description of the present invention is susceptible to various modifications, changes and adaptations, and the same are intended to be comprehended within the meaning and range of equivalents of the appended claims.

What is claimed is:

1. A slotted slide plate assembly for setting bones in a fracture area and exerting a pressure in a predetermined direction to obtain a bone compression, comprising
    (a) a first plate element having a topside and an underside; said underside being adapted for a face-to-face engagement with a bone surface;
    (b) a first throughgoing slide slot provided in said first plate element; the first slide slot having a length oriented parallel to said predetermined direction;
    (c) a first slide ramp bounding said first slide slot and being oriented in said predetermined direction; said first slide ramp being inclined towards said underside in said predetermined direction;
    (d) a second plate element having a topside and an underside; said underside of said second plate element being adapted for a face-to-face engagement with the topside of said first plate element;
    (e) fitting means in said first and second plate elements for preventing a relative displacement, in said predetermined direction, between said first and second plate elements when said first and second plate elements are in a face-to-face engagement with one another;
    (f) a second throughgoing slide slot provided in said second plate element; the second slide slot having a length oriented parallel to said predetermined direction; said second throughgoing slide slot overlapping said first slide slot when said first and second plate elements are in a face-to-face engagement with one another; said first and second slide slots forming a slide slot pair;
    (g) a second slide ramp bounding said second slide slot and being oriented in said predetermined direction; said second slide ramp being inclined towards said underside of said second plate element in said predetermined direction; said first slide ramp being in alignment with and being a continuation of said second slide ramp when said first and second plate elements are in a face-to-face engagement with one another, whereby a tightening screw inserted through said slide slot pair from said topside of said second plate element slides, while being screwed into the bone, with a screw head on said second slide ramp and subsequently on said first slide ramp in said predetermined direction.

2. A slotted slide plate assembly as defined in claim 1, wherein said second slide slot is sufficiently wide at a lower end of said second slide ramp for allowing a head of a tightening screw to pass from the lower end of said second slide ramp to an upper end of said first slide ramp during a screw tightening operation.

3. A slotted slide plate assembly as defined in claim 1, wherein said first slide ramp has an initial length portion and an adjoining terminal length portion; said terminal length portion being situated closer to said underside of said first plate element than said initial length portion and having a lesser slope than that of said initial length portion.

4. A slotted slide plate assembly as defined in claim 3, wherein said slot pair is a first slot pair; further comprising
    (a) a third throughgoing slide slot provided in said first plate element and being spaced from the first slide slot; the third slide slot having a length oriented parallel to said predetermined direction;
    (b) a third slide ramp bounding said third slide slot and being oriented in said predetermined direction; said third slide ramp being inclined towards the underside of said first plate element in said predetermined direction; wherein said third slide ramp has an initial length portion and an adjoining terminal length portion; said terminal length portion of said third slide ramp being situated closer to said underside of said first plate element than said initial length portion of said third slide ramp and having a lesser slope than that of said initial length portion of said third slide ramp;
    (c) a fourth throughgoing slide slot provided in said second plate element and being spaced from said second slide slot; the fourth slide slot having a length oriented parallel to said predetermined direction; said fourth throughgoing slide slot overlapping said third slide slot when said first and second plate elements are in a face-to-face engagement with one another; said third and fourth slide slots forming a second slide slot pair; and (d) a fourth slide ramp bounding said fourth slide slot and being oriented in said predetermined direction; said fourth slide ramp being inclined towards said underside of said second plate element in said predetermined direction; said third slide ramp being in alignment with and being a continuation of said fourth slide ramp when said first and second plate elements are in a face-to-face engagement with one another, whereby a tightening screw inserted through said second slide slot pair from said topside of said second plate element slides, while being screwed into the bone, with a screw head on said fourth slide ramp and subsequently on said third slide ramp in said predetermined direction, simultaneously causing travel of an earlier-tightened screw along said terminal length portion of said first slide ramp.

5. A slotted slide plate assembly as defined in claim 1, wherein said fitting means comprises a projection extending from the underside of said second plate element and an aperture provided in the topside of said first plate element; said aperture form-fittingly receiving said projection when said first and second plate elements are in a face-to-face engagement.

6. A slotted slide plate assembly as defined in claim 5, wherein said aperture constituting a third slide slot bounded by a third ramp, both oriented in said predetermined direction; said third slide slot being covered by said second plate element when said first and second plate elements are in a face-to-face engagement with one another and said third slide slot being adapted to receive a tightening screw after said second plate element is removed from said first plate element.

7. A slotted slide plate assembly as defined in claim 1, further comprising a third slide slot bounded by a third ramp, both oriented in said predetermined direction; said third slide slot being covered by said second plate element when said first and second plate elements are in a face-to-face engagement with one another and said third slide slot being adapted to receive a tightening screw after said second plate element is removed from said first plate element.

8. A slotted slide plate assembly as defined in claim 1, wherein said first plate element has an angled terminal part.

9. A slotted slide plate assembly as defined in claim 1, wherein said first and second plate elements are curved such that the radius of curvature of the topside of the first plate element equals the radius of curvature of the underside of the second plate element.

* * * * *